United States Patent [19]
Horiuchi et al.

[11] Patent Number: 5,561,517
[45] Date of Patent: Oct. 1, 1996

[54] METHOD AND APPARATUS FOR FLOW TYPE PARTICLE IMAGE ANALYSIS USING A PULSE LIGHT EMITTED AT ANY OF AN ODD AND EVEN IMAGE FIELD READING-OUT PERIOD

[75] Inventors: Hideyuki Horiuchi, Abiko; Norio Oowada, Katsuta; Hideki Asai, Mito; Ryohei Yabe, Katsuta, all of Japan

[73] Assignee: Hitachi, Ltd., Tokyo, Japan

[21] Appl. No.: 303,236

[22] Filed: Sep. 8, 1994

[30] Foreign Application Priority Data

Sep. 17, 1993 [JP] Japan .................. 5-230673

[51] Int. Cl.⁶ .................................. G01N 15/14
[52] U.S. Cl. .................................. 356/39; 356/73
[58] Field of Search .................. 356/23, 72, 73, 356/39

[56] References Cited

FOREIGN PATENT DOCUMENTS

| | | |
|---|---|---|
| 466168A2 | 1/1992 | European Pat. Off. . |
| 543514A2 | 5/1993 | European Pat. Off. . |
| 553951A1 | 8/1993 | European Pat. Off. . |
| 556971A2 | 8/1993 | European Pat. Off. . |
| 57-500995 | 6/1982 | Japan . |
| 60-260830 | 12/1985 | Japan . |
| 63-94156 | 4/1988 | Japan . |
| 63-231244 | 9/1988 | Japan . |
| 1-245131 | 9/1989 | Japan . |
| 4-72554 | 3/1992 | Japan . |

*Primary Examiner*—Vincent P. McGraw
*Attorney, Agent, or Firm*—Fay, Sharpe, Beall, Fagan, Minnich & McKee

[57] ABSTRACT

A method and an apparatus for flow type particle image analysis generate a pulse light emission in any one of the odd and the even field image reading-out periods, and multiple exposure is prevented by prohibiting the next pulse light emission in the predetermined period after the emission. The method includes the steps of flowing a sample liquid in a flow cell, detecting particles passing through the flow cell by a laser beam, making a flash lamp emit light after the predetermined period from the particle detection, picking up a particle still image by a TV camera, and further preventing the multiple exposure by providing emission-prohibiting periods which are established by controlling the timings of flash lamp emission and image transfer with the TV camera, a flash lamp emission control circuit, and an image processing control circuit which are controlled by a central control part.

31 Claims, 3 Drawing Sheets

FIG. 1

METHOD AND APPARATUS FOR FLOW TYPE PARTICLE IMAGE ANALYSIS USING A PULSE LIGHT EMITTED AT ANY OF AN ODD AND EVEN IMAGE FIELD READING-OUT PERIOD

BACKGROUND OF THE INVENTION

1. Field of the Invention

The present invention relates to a method and an apparatus for flow type particle image analysis which picks up still images of particles suspended in a sample liquid flow and analyzes the particles picked up in the images, particularly suitable for the particle image analysis of cells or particles in urine or blood.

2. Description of the Related Art

Conventionally, analyzing and classifying corpuscles in blood or cells and particles in urine are done by observing a sample applied on a slide glass with a microscope. In case of urine, since the density of particles is low in urine, a sample is observed after being enriched by a centrifugal separator.

The observation and inspection of particles are automated by using an apparatus in which such a sample as a drop of blood is set at a stage of a microscope after being applied on a slide glass and the stage of the microscope is automatically scanned. Then, the scanning is stopped at the position where the presence of particles is found, and a still image of the particles is picked up. Then the particles in the still image are analyzed and classified by a feature extraction means and a pattern recognition means used in an image processing technique.

The above-mentioned observation and inspection need much time for making a sample, and require difficult work for finding particles by mechanically moving the stage of a microscope to move the particles into an adequate view position of an image pickup region, whereby much time for analysis and a complicate mechanical structure of the apparatus are needed.

As another conventional technique, a flow cytometer method is known. The method optically analyzes a sample which is not applied on a slide glass but flowed in a flow cell where the particles are suspended in the flowing sample.

The method using the flow cytometer observes the strength of fluorescence or scattered light from each particle in the sample and has the ability of analyzing thousands of particles a second.

However, it is difficult to observe feature parameters reflecting a morphological feature of a particle by the method. Therefore, the method cannot classify particles based on the morphological feature as in the conventional microscope method.

As a technique of analyzing and classifying each particle image in a picked up still image of particles in continuous sample flow, techniques described in National Publication for Japan No.500995/1982, and Japanese Patent Application Laid-open No.94156/1988 and No.72554/1992 are known.

The technique described in National Publication for Japan No.500995/1982 devises a method for picking up still images of particles in a sample liquid passing through a special shape of a flow path widening at an image pickup region, by using a flash lamp, and for analyzing the particles in the particle still images.

In the above-mentioned technique, when a particle image enlarged by a microscope is projected on a CCD camera, the flash-lamp pulse light source periodically emits light in synchronizing with the operation of the CCD camera.

The particle still images can be obtained though the particles continuously flow since the emission time of the pulse light source is very short and the CCD camera can pick up 30 pieces of particle still images a second.

In the technique described in Japanese Patent Application Laid-Open No.94156/1988, a particle detection system other than an image pickup system is provided upstream of a particle image pickup region in the sample flow. A particle passing through a flow cell is detected in advance by the particle detection system and a flash lamp emits light at a suitable timing when the particle just passes through a particle image pickup region in the above-mentioned technique.

The technique, without a periodic flash and lamp emission, picks up a particle still image only when a particle is detected, and efficiently accumulates the particle still images. Thus, the technique can avoid picking up a meaningless image having no particle even if the particle density of a sample is low.

Example techniques in which a particle detection part is separately provided in an ordinary flow cytometer and a particle still image is not picked up are described in Japanese Patent Application Laid-Open No.260830/1985, No.231244/1988 and No.245131/1989.

In a flow type particle image analysis apparatus, it is generally necessary to provide a particle detection system in a particle image pickup region or upstream of the region as described in the above-mentioned Japanese Patent Application Laid-Open No.94156/1988 in order to efficiently classify plural kinds of particles in a sample by analyzing still images of particles in a continuous sample flow.

That is, the particle still image is picked up by emitting light from a pulse light source only when a particle passes through a flow cell. This method causes the increase of the sample number to be processed, the reduction of processing time and the improvement of analysis accuracy.

Conventionally, the particle detection is performed by a method of focusing and radiating a laser beam on the sample flow to be analyzed in a flow cell and detecting the light scattered from particles intersecting the laser beam. The scattered light produces a light signal having a strength proportional to an effective scattering cross section of a particle.

The light signal is converted to an electrical signal. The strength of the light signal is affected by the optical refractive index, the optical absorption coefficient, the size and the internal state of a particle, the scattered light detection conditions and so on.

Further, another method of particle detection by forming a particle image on a line image sensor and processing the image is also used for the particle detection.

However, there are the below-mentioned problems in the method of classifying plural kinds of particles in a sample by analyzing the still images of particles in a continuous sample flow.

In the above-mentioned method, the particle images are converted to electrical signals by a TV camera and the arriving time of a particle passing through the particle detection region is random.

Further, one frame of image signals is read out from a CCD TV camera by dividing the frame into two fields of images, namely, an odd field image and an even field image, and taking out the images as electrical signals. The image taking out timing does not depend on the particle arriving detection.

The electric charge accumulated in a photosensitive part of the CCD TV is once transferred to a storage part and the field images are output as the image signals in turn from the storage part.

One pulse signal for reading out a field image is generated according to vertical synchronizing signals. It causes a problem to start picking up the next image, that is, to make a flash lamp emit light for picking up a particle image, when the next particle is detected before two successive pulses for reading out two field images are generated.

If the next image is picked up before two successive pulses for reading out two field images are generated, a double exposure is caused since the transfer of the previous frame image is not completed yet.

In order to resolve the problem, the technique described in Japanese Patent Application Laid-Open No.72544/1992 sets the stroboscope emission timing only during the even field image reading out period and prohibits a flash lamp from emitting light during the odd field image reading out period. That is, the particle detection is permitted only during the even field image reading out period and suppressed during the odd field image reading out period in which the light emission of a flash lamp is prohibited.

Therefore, even if a particle exists in the image pickup region during the odd field image reading out period, a particle image is not picked up since the light emission of a flash lamp is not generated. Then, although the method does not cause a problem if the particle density of an analyzed sample is high and the light emission of a flash lamp is generated in every even field image reading out period, it is probable that a particle image cannot be picked up in spite of the chance for picking up a particle image if the particle density of an analyzed sample is low, since the light emission of a flash lamp is not generated on the chance.

Even if the particle detection system is provided and the number of particles to be processed in a unit time is reduced, it does not sufficiently improve the accuracy of analyzing the sample of low particle density, and also causes the problem of low processing efficiency.

Usually, a field image reading out pulse signal is generated in tens of us after a vertical synchronizing signal, and its width is narrow unlike the vertical synchronizing signal.

Generally, the light emission of a flash lamp is prohibited during the predetermined period before the field image reading out pulse signal is generated in order to prevent multiple exposure of a CCD TV camera. The multiple exposure cannot be sufficiently prevented by prohibiting the light emission of a flash lamp only during the above-mentioned period.

Then, another period of prohibiting the light emission following the above-mentioned period is necessary to transfer the electric charge of one field image accumulated in the photo-electric element of a CCD TV camera to a vertical register in synchronism with the vertical synchronizing signal.

The "another period" is a period in which the accumulated electric charge is transferred to the vertical register and the photo-electric element returns to the state capable of accumulating electric charge.

The light emission during the above-mentioned period results in the superposition of a new image on the image to be transferred and in failing to accumulate the electric charge of a normal image signal, whereby a problem that the light emission of a flash lamp must be prohibited during the above-mentioned period is caused.

SUMMARY OF THE INVENTION

OBJECTS OF THE INVENTION

The present invention has been achieved in consideration of the above-described problems, and the first object of the present invention is to provide a method and an apparatus for flow type particle image analysis in which, for any given sample to be analyzed, a timing signal for the light emission of a pulse light source is generated in every field image reading out period if a chance of particle image pickup occurs, a particle still image is picked up and the light emission is prohibited during the predetermined period after the emission of the pulse light source in order to prevent a multiple exposure. The second object of the present invention is, in order to solve the above-mentioned problem peculiar to the image pickup device (for example, a CCD TV camera), to provide a method and an apparatus for particle image analysis in which a stable particle still image can be obtained by prohibiting the emission of a pulse light source during the predetermined period before and after the transfer of an image in a CCD TV camera and making the pulse light source emit light after the above-mentioned predetermined period.

METHODS FOR SOLVING THE PROBLEMS

For achieving the first object of the present invention, the present invention provides a first method of flow type particle image analysis by flowing, in a flow cell a liquid sample in which particles are suspended, detecting a particle passing through a particle detection region in the flow cell, making a pulse light source emit light at a field image reading out period in which a particle is passing through an image pickup region, picking up a particle still image with an image pickup device by the light emission, reading out and storing the particle still image, analyzing the stored still image, and morphologically classifying the particle, comprising the steps of:

making the pulse light source emit light at any field image reading out period of the image pickup device; and setting the first emission prohibiting period to prohibit the emission of the pulse light source until two successive pulses for reading out two fields of image signals are generated after the emission of the pulse light source.

For achieving the first object of the present invention, the present invention provides a first apparatus for flow type particle image analysis having a particle detection part for flowing, in a flow cell a liquid sample in which particles are suspended, and for detecting a particle passing through a particle detection region in the flow cell, a pulse light source for emitting light at a field image reading out period in which a particle is passing through an image pickup region, an image pickup device for picking up a particle still image by the light emission, a particle image memory for reading out and storing the particle still image, and an analysis part for analyzing the stored particle still image and for morphologically classifying the particle, comprising means for making the pulse light source emit light at any field image reading out period; and means for setting the first emission prohibiting period to prohibit the emission of the pulse light source until two successive pulses for reading out two fields of image signals are generated after the emission of the pulse light source.

For achieving the second object of the present invention, the present invention provides a second method of flow type particle image analysis by flowing, in a flow cell a liquid sample in which particles are suspended, detecting a particle passing through a particle detection region in the flow cell, making a pulse light source emit light at a field image reading out period in which a particle is passing through an image pickup region, picking up a particle still image with an image pickup device by the light emission, reading out and storing the particle still image, analyzing the stored particle still image, and morphologically classifying the particle, comprising the steps of:

setting the second emission prohibiting period to prohibit the emission of the pulse light source during an unstable image pickup period before and after reading-out the particle still image and including the image reading out time itself.

The second method of flow type particle image analysis further includes the step of delaying the emission time of the pulse light source after the second emission prohibiting period if a particle passes through the image pickup region.

The second method further includes the step of cancelling the emission of the pulse light source even if a particle passes through the image pickup region.

The above-mentioned first and second methods further include the steps of:

determining whether each of two successive pulse signals for reading out two field of the particle still image signals is for an even field or an odd field; and storing each of the two fields of the particle still image signals in a predetermined one of two different line memories based on the above-mentioned determination.

Furthermore, the above-mentioned first and second methods include the step of setting the recovering period for emission of the pulse light source shorter than one field image reading out period.

For achieving the second object of the present invention, the present invention provides a second apparatus for flow type particle image analysis having a particle detection part for flowing, in a flow cell, a liquid sample in which particles are suspended, and for detecting a particle passing through a particle detection region in the flow cell, a pulse light source for emitting light at a field image reading out period in which a particle is passing through an image pickup region, an image pickup device for picking up a particle still image by the light emission, a particle image memory for reading out and storing the particle still image, and an analysis part for analyzing the stored still image and for morphologically classifying the particles, comprising:

means for setting the second emission prohibiting period to prohibit the light emission of the pulse light source during an unstable image pickup period before and after reading out the particle still image and including the image reading-out time itself.

The second apparatus further includes means for delaying the light emission time of the pulse light source after the second emission prohibiting period if a particle passes through the image pickup region.

The second apparatus further includes means for cancelling the light emission of the pulse light source even if a particle passes through the image pickup region.

The above-mentioned first and second apparatuses further include;

means for determining whether each of the two successive pulse signals for reading out two fields of the particle still image signals is for an even field or an odd field; and means for storing each of the two fields of the particle still image signals in a predetermined line memory of two different line memories based on the above-mentioned determination.

Furthermore, the above-mentioned first and second apparatuses include means for setting the recovering period for emission of the pulse light source shorter than one field image reading-out period.

In the above-mentioned first and second apparatuses, the particles to be analyzed maybe living cells.

Further in the above-mentioned first and second apparatuses, the particles to be analyzed maybe blood corpuscles.

Moreover in the above-mentioned first and second apparatuses, the particles to be analyzed maybe sedimentation components in urine.

In the following, the features of the present invention are explained in detail.

A CCD TV camera is used as an image pickup device. A particle detection signal is generated every time a particle passes through the particle detection region. The pulse light emission is delayed by a predetermined time after the particle detection signal is generated, and started when the particle arrives at a predetermined position of the image pickup region of the TV camera. Timing of the pulse light emission is the same in both of the odd and the even fields.

After the pulse light emission, the images of the odd and the even fields one constituting image frame of image are taken out as electrical image signals. Then, pulse light emission is prohibited during the period from the pulse light emission to the completion of the two successive pulse generations for reading out images of the two fields even if the next particle arrives at the predetermined position of the image pickup region. The above-mentioned period is set as the first emission prohibiting period.

The field image reading-out pulse is generated in tens of us after the vertical synchronizing signal is output, and its width is narrow.

During a predetermined period before the field image reading-out pulse is generated, a pulse light emission is prohibited in order to prevent multiple exposure of the CCD TV camera.

Generally, it requires a definite period that the electric charge accumulated in a photo-electric element of the CCD TV camera for a time is transferred to a vertical register by one field of image in synchronizing with the vertical synchronizing signal and the photo-electric element again returns to the state capable of accumulating the electric charge of an image.

If a pulse light emission is generated in the above-mentioned definite period, new image signals are superimposed on the electric charge which is being transferred, or the electric charge of normal image signals are not accumulated. Then, in the above-mentioned definite period as well as the predetermined period before the field image reading-out pulse is output, a pulse light emission is to be prohibited. The two periods are together set as the second emission prohibiting period.

In case a particle arrives at the predetermined position of the image pickup region by the TV camera and a chance of pulse light emission occurs, there are two corresponding methods; that is, a method of delaying the pulse light emission after the second emission prohibiting period, and a method of neglecting the chance due to the very short time of the second emission prohibiting period.

The method of delaying the pulse light emission requires that the object particle exist in the image pickup region by the TV camera and, therefore, the velocity of the sample flow should be lower than a definite value.

As mentioned above, the field image reading-out pulse signal is generated at random in the odd field or the even field image reading-out period according to the time at which the particle arrives at the predetermined position of the image pickup region by the TV camera. Then, for storing the particle image signals in the image memory, the image of the odd field image should be stored in the odd line of the image memory, and the image of the even field image in the even line of the image memory.

If the above-mentioned procedures are not kept, the data of the image memory of the odd line and that of the image memory of the even line are exchanged and the image processing is not correctly executed.

Then, assuming that each scanning line of the TV camera corresponds one-to-one with a line of the image memory, in order to keep the procedures, it should be decided in which line of the image memory, the image signals are stored, (in the odd or the even line), by judging the generated timing of the reading-out pulse, that is, the pulse for the odd field or the pulse for the even field.

Since the minimum value of the first emission prohibiting period is one field image reading-out period, the energy for one pulse light emission needs to be sufficiently accumulated as an electric charge in a condenser of the pulse light source. Then, it is necessary that the minimum time for the recovery period of emission ability of the pulse light source is less than one field image reading-out period.

By the first feature achieving the first object of the present invention, the timing of the pulse light emission is possible at both of the odd and the even field image reading out periods and a still image of the particle arriving at the particle detection system at random can be picked up. The two successive fields of picked-up images can be read out in turn from the field image which corresponds to the field image reading-out period following the pulse light emission.

Furthermore, multiple exposures can be prevented since the next pulse light emission can be prohibited until two successive pulses for reading-out the odd and the even images are generated after the pulse light emission.

By the second feature achieving the second object of the present invention, the pulse light is not emitted even though the timing of the pulse light emission occurs in the second emission prohibiting period, and the unstable operations of the image pickup device can be prevented since the unstable image pickup period before and after the transfer of the electric image signals accumulated in the image pickup device is set as the second emission prohibiting period.

If picking up a particle still image in the second emission prohibiting period iS desired, the pulse light emission is to be delayed right after the second emission prohibiting period and the stable still image can be picked up, whereby the image processing can be accurately performed.

By taking the assumption that the second emission prohibiting period is sufficiently short, the pulse light emission can be cancelled after the delay, whereby the pickup of unstable images can be prevented as well.

By the first and second features of the present invention, the field to be read out is judged as either the odd or the even field, and it is controlled based on the judgement in which line of the image memory the image signal is to be written, (in the odd or the even line), since the field image reading-out is started at random. By the above-mentioned control, exchange between the image signals to be stored fin the odd line and those in the even line is prevented and the particle still image is correctly stored in the image memory. Thereby, the particle image processing of classifying the particles is also correctly executed.

The light strength of the pulse light emission can be kept constant since the pulse light source is sufficiently charged in the above-mentioned emission timing by using a pulse light source capable of emitting light by the emission period of less than one field image reading-out period.

DETAILED DESCRIPTION OF THE EMBODIMENTS

Hereinafter, details of the present invention are explained based on preferred embodiments. Embodiments of a method and an apparatus for particle image analysis by the present invention are explained referring to FIGS. 1, 2 and 3 in the following.

Figure 1:
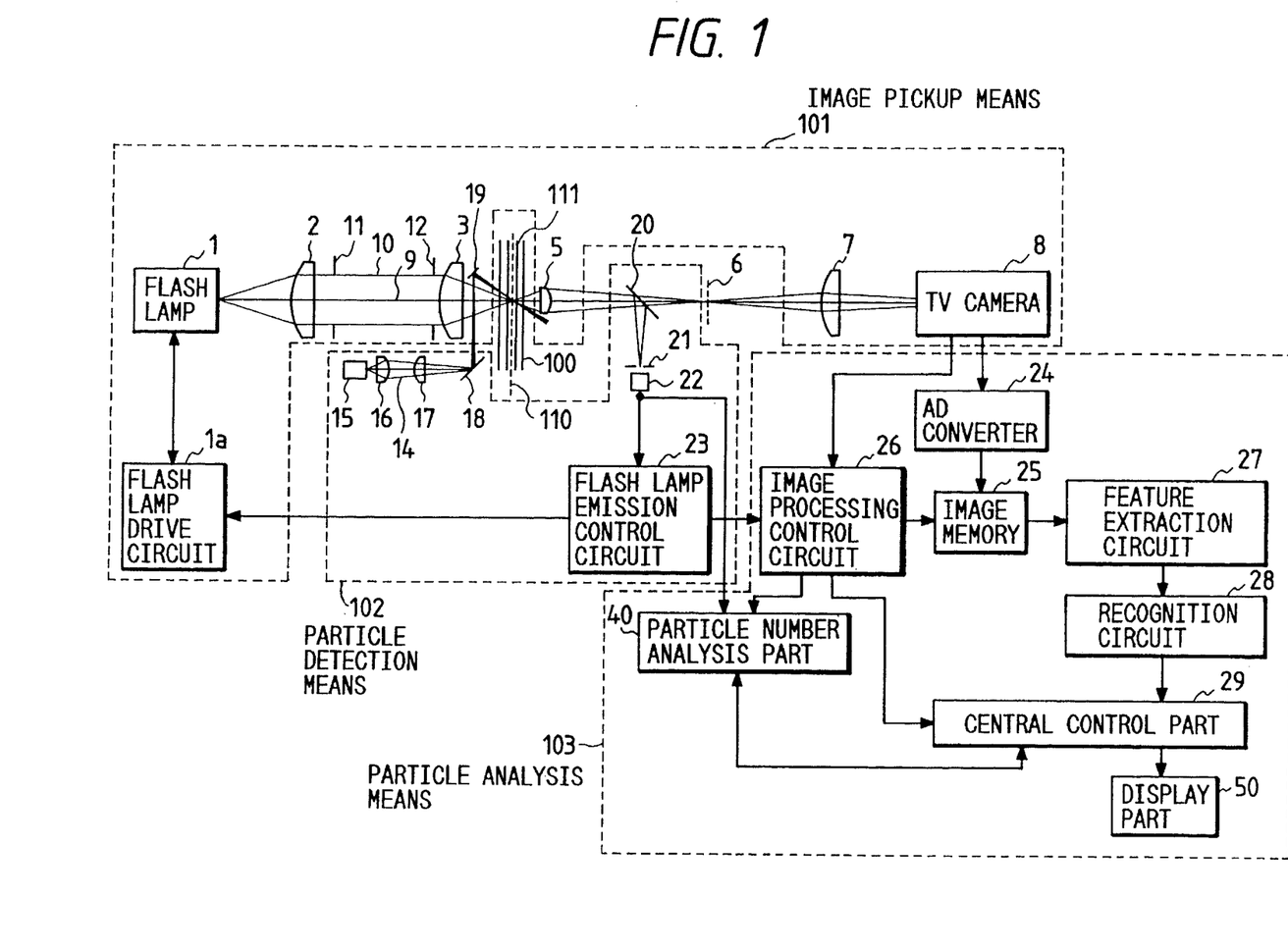
FIG. 1 is a conceptual constitution diagram of an embodiment of a method and an apparatus for flow type particle image analysis by the present invention.

As shown in FIG. 1, the apparatus for flow type particle image analysis comprises a flow cell 100 for a liquid sample in which particles are suspended, image pickup means 101, a particle detection means 102 and a particle analysis means 103.

Sample liquid 110 and sheath liquid 111 are together flowed into the flow cell 100, and the sample liquid 110 is covered by the sheath flow 111.

Then, the sample liquid flow 110 becomes the stable stationary flow, namely, sheath flow in the direction vertical to the optical axis of the image pickup means (the optical axis of a microscope) having the flat cross section and flowing in the center of the flow cell 100 from the top to the bottom of the page. The velocity of the sample liquid flow 100 is controlled under the conditions set by a central control part 29.

The image pickup means 101 has the function of a microscope and comprises a flash lamp 1 as a pulse light source, a flash lamp drive circuit 1a for making the flash lamp 1 emit light, a field lens 2 for making the pulse light 1 a parallel beam, and a microscope condenser lens 3 for condensing the parallel light beam on the sample liquid flow 110. The image pickup means further comprises a microscope object lens 5 for focusing the pulse beam on the sample liquid flow 110 in the flow cell 100 at the position of image formation 6 as an image of a particle, a TV camera 8 for picking up and converting the image of a particle at the position of image formation 6 to electrical signal data of the image, and a visual field diaphragm 11 and an aperture diaphragm 12 for restricting the width of the pulse beam.

A CCD camera with small afterimage effect is generally used as the TV camera.

The particle detection means 102 comprises a semiconductor laser 15 for emitting a laser beam used for the particle detection, a collimator lens 16 for forming the laser beam from the semiconductor laser 15 as a parallel beam 14, a cylindrical lens 17 for passing only the component in one direction of the laser beam from the collimator lens 16, a reflection mirror 18 for reflecting the light beam from the cylindrical lens 17, and a micro-reflection-mirror 19 provided between the microscope condenser lens 3 and the flow cell 100 for guiding the laser beam from the micro-reflecting-mirror 18 to the near upstream side of a particle image pickup region of the sample liquid flow 110. The particle detection means 102 further comprises a microscope object lens 5 (commonly used for the microscope object lens 5 of the particle image pickup means 101) for condensing a part of the laser beam scattered by the particle, a beam splitter 20 for reflecting the scattered light condensed by the microscope object lens 5, a photo-detection circuit 22 for receiving the scattered light from the beam splitter 20 via the diaphragm 21 and for outputting an electrical signal corresponding to the strength of the scattered light, and a flash lamp emission control circuit 23 for operating the flash lamp drive circuit 1a.

The particle analysis means comprises an AD converter 24 for converting the signals of the image data transmitted from the TV camera 8 to digital signals, an image memory 25 for storing the data from the AD converter 24 in the predetermined addresses, an image processing control circuit 26 for controlling the writing-in and the reading-out of the data stored in the image memory 25, a feature extraction circuit 27 and a recognition circuit 28 for executing the image processing of the data from the image memory 25 and for counting and classifying the particles, and a central control part 29 for setting the conditions of the image pickup by the TV camera 8 and the sample liquid flow 110, for controlling the image processing control circuit 26, for memorizing the image processing results from the recognition circuit 28, for sending and receiving the data by the particle number analysis part 40 and for displaying the image processing results on a display part 50.

The process of the method and operations of the apparatus for flow type particle analysis by the present invention are explained referring to FIG. 1.

The semiconductor laser 15 is continuously oscillated and the passing of particles in the particle detection region of the sample liquid flow 110 is continuously monitored. The laser beam from the semiconductor laser 15 is formed as the parallel laser beam 14 by the collimator lens 16 and a component in one direction of the beam is condensed by the cylindrical lens 17.

The laser beam is reflected by the reflection mirror 18 and the micro-reflection-mirror 19 and applied to the sample liquid flow 110.

The application position of the laser beam is the position for particle detection at the neighborhood in the upstream side of the image pickup region in the sample liquid flow 110 on which the laser beam 14 is focused by the cylindrical lens 17.

The laser beam is scattered when a particle to be measured intersects the laser beam. Then it is reflected by the beam splitter 20, received by the photo-detection circuit 22, and converted to an electrical signal corresponding to the strength of the scattered beam.

The electrical signal of particle detection is judged on the basis of whether the signal has a signal level more than the predetermined level. If the level is more than the predetermined value, the particle is judged as the particle to be processed in the image processing, and the detection signal of the particle is transmitted to the flash lamp emission control circuit 23 and the particle number analysis part 40.

The flash lamp emission control circuit 23 generates an emission signal of the flash lamp so that the flash lamp 1 emits light and an image of the particle is picked up right when the particle arrives at the predetermined position of the particle image pickup region.

That is, the emission timing of the flash lamp 1 is determined on the basis of the generation timing of the field signals of the TV camera, and the particle detection signal is delayed by the delay time to be determined from the distance between the particle detection position and the particle pickup region, and from the velocity of the sample liquid flow 110.

Then, the flash lamp emission generating signal is generated and output to the flash lamp drive circuit 1a.

Meanwhile, the accuracy of the particle detection and analysis is not affected by the velocity and the particle density of the sample liquid flow 110 since the delay time is very short due to the very short distance between the particle detection position and the particle image pickup region.

The flash lamp drive circuit 1a makes the flash lamp emit light when the flash lamp emission generating signal is transmitted to the flash lamp drive circuit 1a. The pulse light emitted by the flash lamp 1a advances on the microscope light axis 9, made parallel by the field lens 2, condensed by the microscope condenser lens 3 and applied on the sample liquid flow 110 in the flow cell. Then, the width of the pulse beam 10 is restricted by the visual field diaphragm 11 and the aperture diaphragm 12.

The pulse beam applied on the sample liquid flow 110 in the flow cell 100 is condensed by the microscope object lens 5 and forms an image at the position of image formation 6. The image at the position of image formation 6 is projected on an image pickup screen of the TV camera 8 and converted to image data signals. Then, a particle still image pickup is accomplished. The conditions of image pickup are stored in the central control part 29 in advance and the image pickup operations of the TV camera are controlled under the stored conditions.

The image data signals output from the TV camera 8 are converted to digital signals by the AD converter 24 and the digital signals are memorized at the predetermined addresses of the image memory 25 under the control of the image processing control circuit 26.

The data memorized in the image memory 25 are read out and input into the feature extraction circuit 27 and the recognition circuit 28 under the control of the image processing control circuit 26. Then, the image processing of the data is executed and the image processing results are stored in the central control part 29. The stored data are classification results of the particles and feature parameters for recognizing the particles.

The particle classification processing is automatically executed by a conventional pattern recognition method. The image processing results, the measurement conditions and the number information of the processed images are transmitted from the central control part 29 to the particle number analysis part 40.

In the particle number analysis part 40, the correspondence relations between the detected particle and the particle classification results are examined and the classification and recognizing results of the particle images are finally arranged.

Figure 2:
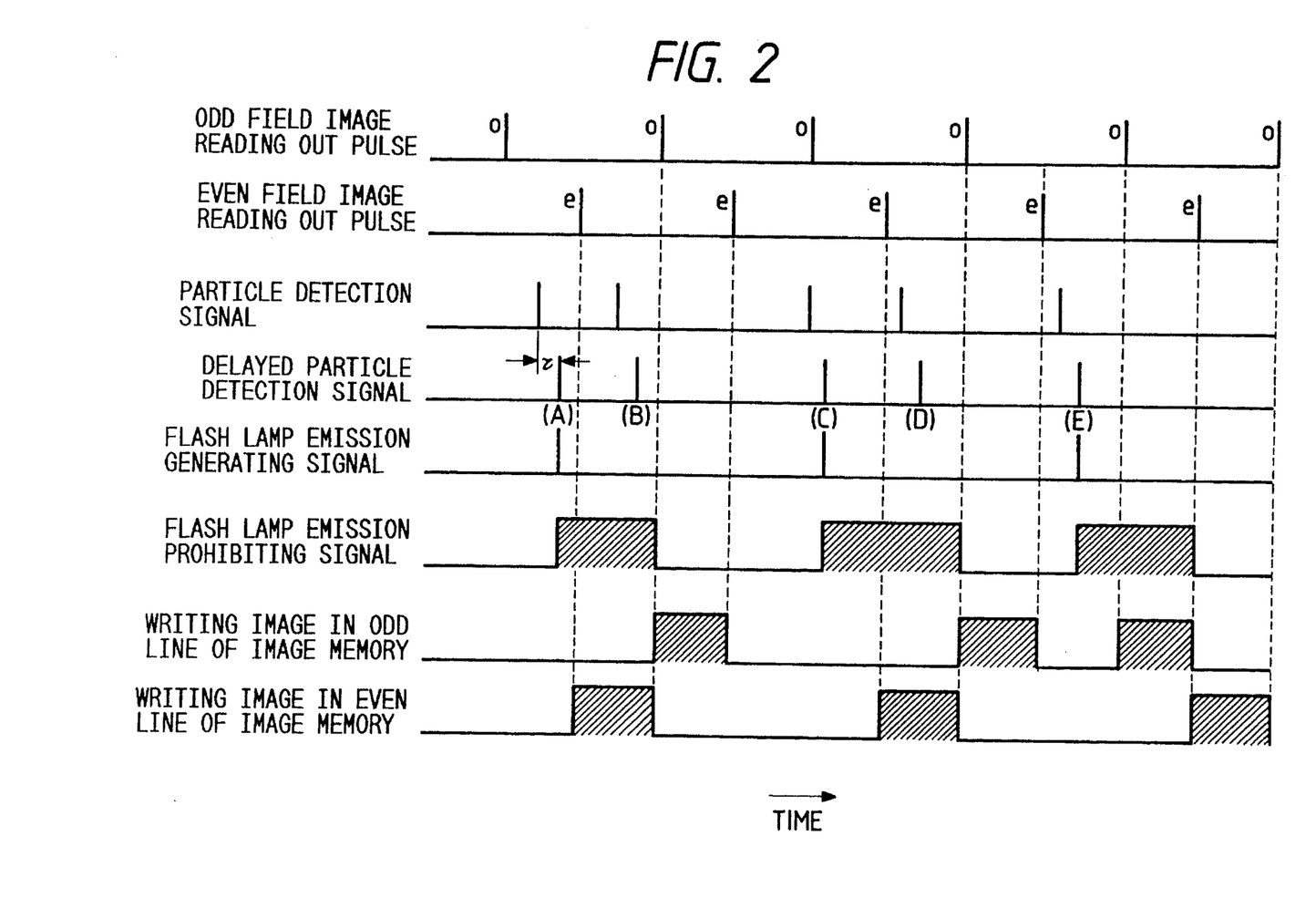
FIG. 2 is a graph showing the timing of the first emission prohibiting period of the embodiment shown in FIG. 1.

The first emission prohibiting period for prohibiting the emission of the flash lamp in the method of flow type particle image analysis by the present invention are explained by referring to FIG. 2.

As shown in FIG. 2, the reading-out pulses of the odd field image and the even field image are alternately generated.

The scattered light from the particle passing through the particle detection position is detected.

The particle arrives statistically at a random time at the particle detection region. The delayed particle detection signal is generated, which is delayed by the delay time $\tau$ required from the particle detection to the arrival of the particle at the image pickup position by the TV camera. By the delayed particle detection signal, a flash lamp emission generating signal is started.

When the flash lamp emission generating signal is started, two successive field image reading-out signals are output and the flash lamp emission is prohibited by generating a signal designating the first emission prohibiting period during which one frame of particle image is transferred from the TV camera.

The generation timings of the emission generating signals are decided and output by the flash lamp control circuit 23 on the basis of the particle detection signal of the scattered light by the photo-detection circuit 22 and the field image reading-out signal output from the image processing control circuit 26 for processing the images of the TV camera 8.

In FIG. 2, at the time points of the delayed particle detection signals (A), (C) and (E), the light of the flash lamp is emitted, but, at the time points of the delayed particle detection signals (B) and (D), the light emission is prohibited. By the delayed particle detection signals (A) and (C), the field images are read out in the order of the even and the odd field images, and, by the delayed particle detection signal (E), they are read out in the order of the odd and the even field images.

The emission prohibiting signals of the flash lamp have different pulse widths, respectively, each of which is more than one field period and less than two field periods. Therefore, the electric charge for the flash lamp emission must be sufficiently accumulated. Then, the flash lamp drive circuit 1a is required to have the ability of completing the electric charge accumulation within one field period.

The image processing control circuit 26 judges whether the read-out field image is the odd or the even field image, and outputs the image writing in signal for the odd line of the image memory 25 or for the even line of the image memory 25 corresponding to the above-mentioned judgment.

By the above-mentioned function, the field image read out by the odd field image reading-out signal is correctly transferred to the odd line of the image memory 25, and the field image read out by the even field image reading-out signal is correctly transferred to the even line of the image memory 25 so that exchange of the memory lines does not occur even if the field image reading-out starts from any one of the odd and the even fields.

Figure 3:
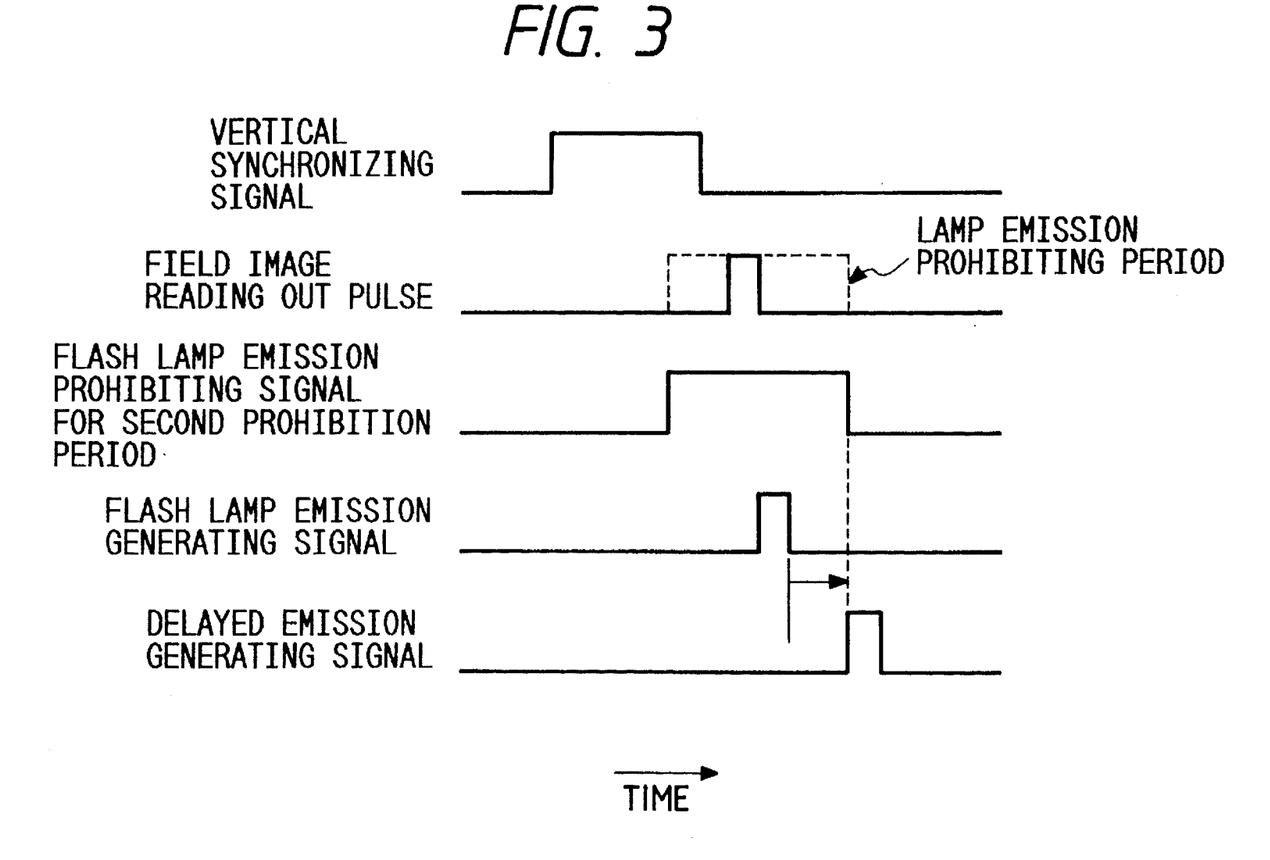
FIG. 3 is a graph showing the timing of the second emission prohibiting period of the embodiment shown in FIG. 1.

The second emission prohibiting period for prohibiting the emission of the flash lamp in the method of flow type particle image analysis by the present invention is explained by referring to FIG. 3.

The field image reading-out signal is generated right after the vertical synchronizing signal. The prohibition period of the lamp emission must be provided before and after the field image reading-out signal due to the operation property of the TV camera.

Generally, the emission prohibiting period of the flash lamp before the field image reading-out pulse is provided to prevent a double exposure, whereby the certain holding and transferring of the picked-up image is established. The second emission prohibiting period is a continuous one since the emission prohibiting period is also set succeeding the emission prohibiting period of the flash lamp before the field image reading-out pulse in the present invention as shown in FIG. 3.

Even if the emission timing of the flash lamp by the particle detection occurs during the second emission prohibiting period of the flash lamp, the lamp emission is prohibited as shown in FIG. 3.

The particle arrival probability during the second emission prohibiting period has a definite value since the particle passing through the particle detection region occurs completely at random.

Therefore, if the above-mentioned emission prohibition period is provided, some countermeasure should be taken to the emission prohibiting period.

In the embodiment shown by FIG. 3, the emission of the flash lamp is delayed right after the second emission prohibiting period in detecting that a particle passes through the particle detection region during the second emission prohibiting period.

A countermeasure of neglecting a particle which passes through the particle detection region during the second emission prohibiting period can be taken since the probability of particle existence in the region during the period can be neglected due to the very short time of the second emission prohibiting period of the flash lamp. The countermeasure is to be taken is decided based on the conditions of the sample.

If the sample is analyzed by plural analysis modes, the above-mentioned processing and apparatus operations are executed in each analysis mode, and the data of results in each analysis mode are integrated and arranged as the final results at the final stage.

The method and the apparatus for flow type particle image analysis by the present invention is effectively applied to the analysis and classification of living things, cells, blood corpuscles, such as red and white corpuscles and sedimentation components of urine.

Although a CCD type camera is used as an example of the image pickup device in the preferred embodiment, the image pickup device is not restricted to the CCD type, and any pickup device having the same functions as the CCD type is applicable.

Further, although the embodiment wherein a flash lamp is used has been explained, other kinds of pulse light sources are also applicable.

As explained in detail above, firstly, it becomes possible by the present invention to present a method and apparatus for flow type particle analysis wherein, for any sample to be analyzed, the timing signal of a pulse light emission is generated at any one of the odd and the even field image reading-out periods when the pickup chance of a particle image occurs, and further the particle image is picked up and multiple exposure is prevented by prohibiting the emission of the pulse light source in the predetermined period after the pulse light emission.

Secondly, it is also possible according to the present invention to present a method and an apparatus for flow type particle analysis, wherein the pulse light emission is prohibited in the predetermined period before and after the image transfer in the image pickup device such as a CCD camera, and further a stable particle still image is picked up and the particle still image is analyzed.

What is claimed is:
1. A method of flow type particle image analysis by flowing, in a flow cell, a liquid sample in which particles are suspended, detecting a particle passing through a particle detection region in said flow cell, making a pulse light source emit light at a field image reading-out period in which a particle is passing through an image pickup region, picking up a particle still image with an image pickup device by the light emission, reading-out and storing said particle still image, analyzing said stored particle still image, and morphologically classifying said particle, said method comprising the steps of:

driving said pulse light source to emit light at any of an odd image field reading-out period and an even image field reading-out period of said image pickup device, said pulse light source being capable of being driven to emit light at an odd image field reading-out period and being capable of being driven to emit light at an even image field reading-out period;

setting a first emission prohibiting period to prohibit said emission of said pulse light source until two successive pulses for reading out two fields of image signals are generated after said emission from said pulse light source; and setting a second emission prohibiting period to prohibit said emission from the pulse light source during a predetermined period before and after reading out said particle still image and including a particle still image reading-out time itself.

2. A method of flow type particle image analysis according to claim 1, further including the step of:

delaying an emission time of said pulse light source after said second emission prohibiting period if at least one particle passes through said image pickup region.

3. A method of flow type particle image analysis according to claim 2, further including the step of:

cancelling said emission from said pulse light source at said delayed emission time.

4. A method of flow type particle image analysis according to claim 1, further including the steps of:

determining whether each of said two successive pulse signals for reading out two fields of particle image signals is for an even field image reading-out or an odd field image reading-out; and storing each one of said two fields of said particle image signals in a respective predetermined line memory of two different line memories based on said determination.

5. A method of flow type particle image analysis according to claim 1, further including the step of:

setting the recovering period for emission of said pulse light source shorter than said any of an odd image field reading-out period and an even image field reading-out period.

6. A method of flow type particle image analysis according to claim 2, further including the steps of:

determining whether each of said two successive pulse signals for reading out two fields of particle image signals is for an even field image reading-out or an odd field image reading-out; and storing each one of said two fields of said particle image signals in a respective predetermined line memory of two different line memories based on said determination.

7. A method of flow type particle image analysis according to claim 4, further including the step of:

setting the recovering period for emission of said pulse light source shorter than said any of an odd field image reading-out period and an even field image reading-out period.

8. A method of flow type particle image analysis according to claim 4, further including the step of:

delaying an emission time of said pulse light source after said second emission prohibiting period if at least one particle passes through said image pickup region.

9. A method of flow type particle image analysis according to claim 8, further including the step of:

cancelling said emission from said pulse light source at said delayed emission time.

10. A method of flow type particle image analysis according to claim 5, further including the step of:

delaying an emission time of said pulse light source after said second emission prohibiting period if at least one particles passes through said image pickup region.

11. A method of flow type particle image analysis according to claim 10, further including the step of:

cancelling said emission from said pulse light source at said delayed emission time.

12. An apparatus for flow type particle image analysis according to claim 2, wherein said particles to be analyzed are living cells.

13. An apparatus for flow type particle image analysis according to claim 2, wherein said particles to be analyzed are blood corpuscles.

14. An apparatus for flow type particle image analysis according to claim 2, wherein said particles to be analyzed are sedimentation components in urine.

15. An apparatus for flow type particle image analysis having a particle detection part for flowing, in a flow cell, a liquid sample in which particles are suspended, and for detecting a particle passing through a particle detection region in said flow cell, a pulse light source for emitting light at a field image reading-out period in which a particle is passing through an image pickup region, an image pickup device for picking up a particle still image by said light emission, a particle image memory for reading out and storing said particle still image, and an analysis part for analyzing said stored particle still image and for morphologically classifying the particle, said apparatus comprising:

means for driving said pulse light source to emit light at any of an odd image field reading-out period and an even image field reading-out period, said driving means being capable of driving said pulse light source to emit light at an odd image field reading-out period and being capable of driving said pulse light source to emit light at an even image field reading-out period;

means for setting a first emission prohibiting period to prohibit said emission of said pulse light source until two successive pulses for reading out two fields of image signals are generated after said emission from said pulse light source; and means for setting a second emission prohibiting period to prohibit said emission from the pulse light source during a predetermined period before and after reading out said particle still image and including a particle still image reading-out time itself.

16. An apparatus for flow type particle image analysis according to claim 15, further including:

means for delaying an emission time of said pulse light source after said second emission prohibiting period if at least one particle passes through said image pickup region.

17. An apparatus for flow type particle image analysis according to claim 16, further including:

means for cancelling said emission from said pulse light source at said delayed emission time.

18. An apparatus for flow type particle image analysis according to claim 15, further including:

means for determining whether each of two successive pulse signals for reading out two fields of particle still image signals is for an even field image reading-out or an odd field image reading-out; and means for storing each of the two fields of said particle still image signals in a respective predetermined line memory of two different line memories based on said determination.

19. An apparatus for flow type particle image analysis according to claim 15, further including:

means for setting a recovering period for emission of said pulse light source shorter than said any of an odd image field reading-out period and an even image field reading-out period.

20. An apparatus for flow type particle image analysis according to claim 15, wherein said particles to be analyzed are living cells.

21. An apparatus for flow type particle image analysis according to claim 15, wherein said particles to be analyzed are blood corpuscles.

22. An apparatus for flow type particle image analysis according to claim 15, wherein said particles to be analyzed are sedimentation components in urine.

23. An apparatus for flow type particle image analysis according to claim 16, further including:

means for determining whether each of two successive pulse signals for reading out two fields of particle still image signals is for an even field image reading-out or an odd field image reading-out; and means for storing each of the two fields of said particle still image signals in a respective predetermined line memory of two different line memories based on said determination.

24. An apparatus for flow type particle image analysis according to claim 18, further including:

means for setting a recovering period for emission of said pulse light source shorter than said any of an odd field image reading-out period and an even field image reading-out period.

25. An apparatus for flow type particle image analysis according to claim 18, further including:

means for delaying an emission time of said pulse light source after said second emission prohibiting period if at least one particle passes through said image pickup region.

26. An apparatus for flow type particle image analysis according to claim 25, further including:

means for cancelling said emission from said pulse light source at said delayed emission time.

27. An apparatus for flow type particle image analysis according to claim 19, further including:

means for delaying an emission time of said pulse light source after said second emission prohibiting period if at least one particle passes through said image pickup region.

28. An apparatus for flow type particle image analysis according to claim 27, further including:

means for cancelling said emission from said pulse light source at said delayed emission time.

29. An apparatus for flow type particle image analysis according to claim 16, wherein said particles to be analyzed are living cells.

30. An apparatus for flow type particle image analysis according to claim 16, wherein said particles to be analyzed are blood corpuscles.

31. An apparatus for flow type particle image analysis according to claim 16, wherein said particles to be analyzed are sedimentation components in urine.

* * * * *